(12) United States Patent
Georgeson et al.

(10) Patent No.: US 10,113,951 B2
(45) Date of Patent: Oct. 30, 2018

(54) APPARATUS, SYSTEMS, AND METHODS FOR INSPECTING A PART

(71) Applicant: The Boeing Company, Chicago, IL (US)

(72) Inventors: Gary E. Georgeson, Tacoma, WA (US); William P. Motzer, Mount Pleasant, SC (US); Jeffry J. Garvey, Mt. Pleasant, SC (US); Scott W. Lea, Renton, WA (US); James C. Kennedy, Summerville, SC (US); Steven K. Brady, Renton, WA (US); Alan F. Stewart, Seattle, WA (US); Jill P. Bingham, Seattle, WA (US)

(73) Assignee: The Boeing Company, Chicago, IL (US)

( * ) Notice: Subject to any disclaimer, the term of this patent is extended or adjusted under 35 U.S.C. 154(b) by 111 days.

(21) Appl. No.: 15/135,703

(22) Filed: Apr. 22, 2016

(65) Prior Publication Data

US 2017/0307516 A1 Oct. 26, 2017

(51) Int. Cl.
*H01J 3/14* (2006.01)
*G01N 21/17* (2006.01)
*G02B 7/24* (2006.01)

(52) U.S. Cl.
CPC .......... *G01N 21/1702* (2013.01); *G02B 7/24* (2013.01); *G01N 2201/068* (2013.01); *G01N 2201/06113* (2013.01)

(58) Field of Classification Search
CPC ........ B61K 9/08; B61K 13/00; B23K 26/128; B23K 37/006
See application file for complete search history.

(56) References Cited

U.S. PATENT DOCUMENTS

| | | | |
|---|---|---|---|
| 9,164,066 B1 | 10/2015 | Bossi et al. | |
| 9,188,566 B2 | 11/2015 | Georgeson et al. | |
| 9,250,213 B1 | 2/2016 | Bossi et al. | |
| 9,383,342 B1 | 7/2016 | Bossi et al. | |
| 2014/0116146 A1 | 5/2014 | Bossi et al. | |
| 2016/0209003 A1* | 7/2016 | Mesher | B61K 13/00 |

OTHER PUBLICATIONS

U.S. Appl. No. 15/056,684.
U.S. Appl. No. 15/070,261.
U.S. Appl. No. 15/070,357.

* cited by examiner

*Primary Examiner* — Thanh Luu
(74) *Attorney, Agent, or Firm* — Kunzler, PC

(57) ABSTRACT

Described herein is an apparatus, for shielding light generated by a laser during non-destructive inspection of an object. The apparatus includes a light shield at least partially enveloping the laser and defining a first opening through which light generated by the laser passes from the laser to the object. The light shield is opaque and includes at least one first biasing mechanism. The apparatus also includes at least one first light seal coupled to the light shield about the first opening of the light shield. The at least one first biasing mechanism is configured to urge resilient deformation of the at least one first light seal against the object. When the at least one first light seal is resiliently deformed against the object, light generated by the laser is constrained within a light containment space defined between the light shield, the at least one first light seal, and the object.

16 Claims, 8 Drawing Sheets

APPARATUS, SYSTEMS, AND METHODS FOR INSPECTING A PART

FIELD

This disclosure relates generally to inspecting an object using non-destructive inspection techniques, and more particularly to shielding light generated by a light source during non-destructive inspection of the object.

BACKGROUND

Non-destructive inspection of an object using a laser light to generate a stress wave in the object and detecting characteristics of the stress wave to determine structural defects in the object are known. Due to the high energy associated with laser lights used in such conventional non-destructive inspection techniques, and the potential for the laser light to be reflected or scattered off of an object and cause bodily harm, objects are traditionally inspected in an enclosed room void of human presence.

SUMMARY

The subject matter of the present application has been developed in response to the present state of the art, and in particular, in response to the shortcomings of conventional apparatuses, systems, and method for non-destructively inspecting objects using laser-induced stress waves, that have not yet been fully solved by currently available techniques. For example, for some large objects, setting aside a room sufficiently large to accommodate the inspection of such large objects, while disallowing the ability of humans to be in the room, such as for performing related or unrelated tasks, is both economically straining and physically impractical. Accordingly, the subject matter of the present application has been developed to provide apparatuses, systems, and methods for shielding light generated by a laser, or other light source, during the non-destructive inspection of an object, that overcome at least some of the above-discussed shortcomings of prior art techniques. For example, in some embodiments, the apparatuses and systems of the present disclosure allow for concurrent use of the same room or space both for the automated inspection of objects, such as large objects, using laser-induced stress waves and for other related or unrelated tasks by personnel in the room.

According to one embodiment, an apparatus, for shielding light generated by a laser during non-destructive inspection of an object, includes a light shield at least partially enveloping the laser and defining a first opening through which light generated by the laser passes from the laser to the object. The light shield is opaque and includes at least one first biasing mechanism. The apparatus also includes at least one first light seal coupled to the light shield about the first opening of the light shield. The at least one first light seal is resiliently flexible and opaque. The at least one first biasing mechanism is configured to urge resilient deformation of the at least one first light seal against the object. When the at least one first light seal is resiliently deformed against the object, light generated by the laser is constrained within a light containment space defined between the light shield, the at least one first light seal, and the object.

In some implementations of the apparatus, the light shield and the at least one first light seal is movable relative to the object when the at least one first light seal is resiliently deformed against the object.

According to certain implementations of the apparatus, the at least one first biasing mechanism of the light shield includes at least one concertinaed sidewall of the light shield.

In yet some implementations, the apparatus also includes a hinge. At least a portion of the light shield is pivotable about the hinge. The at least one first biasing mechanism includes at least one spring configured to pivotally bias the at least a portion of the light shield about the hinge.

In certain implementations, the apparatus additionally includes at least one light sensor. The at least one first light seal is positioned between the at least one light sensor and the first opening defined by the light shield.

According to some implementations of the apparatus, the at least one first light seal is a first inner light seal and a first outer light seal. The first inner light seal being spaced apart from the first outer light seal. The apparatus can further include at least one inner light sensor and at least one outer light sensor. The first inner light seal can be positioned between the at least one inner light sensor and the first opening defined by the light shield. Similarly, the first outer light seal can be positioned between the at least one inner light sensor and the at least one outer light sensor.

In some implementations of the apparatus, the laser is non-movably fixed to the light shield.

According to certain implementations of the apparatus, the laser is movably fixed to the light shield and the light shield is movable relative to the object.

According to some implementations of the apparatus, the light shield includes a first portion that defines the first opening, a second portion that is spaced apart from the first portion and defines a second opening, at least one second biasing mechanism, and a spine coupling together the first portion and the second portion. The apparatus further includes at least one second light seal coupled to the second portion of the light shield about the second opening. The object includes a first surface, a second surface opposing the first surface, and an edge at a convergence of the first surface and the second surface. The at least one first biasing mechanism is configured to urge resilient deformation of the at least one first light seal against the first surface of the object. The at least one second biasing mechanism is configured to urge resilient deformation of the at least one second light seal against the second surface of the object. When the at least one first light seal is resiliently deformed against the first surface of the object and the at least one second light seal is resiliently deformed against the second surface of the object, the light containment space is defined between the light shield, the at least one first light seal, the at least one second light seal, and the object. A light sensor can be fixed relative to the second portion of the light shield, spaced apart from the laser, and aligned to receive light directly from the laser when the light is unobstructed by the object.

In some implementations of the apparatus, the light shield includes a rigid frame and a flexible and an opaque material affixed to the rigid frame.

According to a particular implementation of the apparatus, the light shield has a substantially circular cross-sectional shape and the at least one first light seal has a substantially annular shape.

In one example of the particular implementation, the object can include a first surface, a second surface opposing the first surface, and an edge at a convergence of the first surface and the second surface. The at least one first biasing mechanism may be configured to urge resilient deformation of the at least one first light seal against the first surface of the object. The apparatus can further include a light shield module fixed relative to the laser and movable relative to the light shield. The light shield module includes a bracket positionable to wrap around the edge of the object from the first surface to the second surface, at least one second light seal coupled to the bracket, and at least one second biasing mechanism configured to urge resilient deformation of the at least one second light seal against the second surface of the object.

In another example of the particular implementation, the object can include a first surface, a second surface opposing the first surface, and an edge at a convergence of the first surface and the second surface. The at least one first biasing mechanism can be configured to urge resilient deformation of the at least one first light seal against the first surface of the object. The light shield is a first shield. The apparatus can further include a second light shield that is independently movably relative to the first shield, is opaque, defines a second opening, has a substantially circular cross-sectional shape, and include at least one second biasing mechanism. Additionally, the apparatus may include at least one second light seal coupled to the second light shield about the second opening of second shield. The at least one second light seal is resiliently flexible and opaque. The at least one second biasing mechanism is configured to urge resilient deformation of the at least one second light seal against the second surface of the object. When the at least one first light seal is resiliently deformed against the object and the at least one second light seal is resiliently deformed against the second surface of the object, the light containment space is defined between the first shield, the at least one first light seal, the at least one second light seal, the second shield, and the object.

According to yet another example of the particular implementation, the object includes a first surface, a second surface opposing the first surface, and an edge at a convergence of the first surface and the second surface. The at least one first biasing mechanism is configured to urge resilient deformation of the at least one first light seal against the first surface of the object. The apparatus further includes an opaque light barrier, independently movable relative to the light shield and positionable against the second surface of the object. When the at least one first light seal is resiliently deformed against the first surface of the object and the opaque light barrier is positioned against the second surface of the object, the light containment space is defined between the light shield, the at least one first light seal, the opaque light barrier, and the object.

In another embodiment, a system for non-destructively inspecting an object includes a first robot, a first light shield coupled to the first robot, and a laser coupled to and co-movable with the first light shield. The laser is configured to generate a laser light beam. The system also includes at least one first light seal coupled to and co-movable with the first light shield. The first robot is configured to move the first light shield relative to the object to position the at least one first light seal in contact with the object and form a light containment space defined between the first light shield, the at least one first light seal, and the object.

According to some implementations of the system, the first robot is further configured to move the laser relative to the light shield. The system further includes a light shield module fixed to laser and movable relative to the light shield. The light shield includes a bracket that has a substantially U-shape and at least one second light seal coupled to the bracket. The first robot is configured to position the bracket to wrap around an edge of the object and to position the at least one second light seal in contact with the object such that the light containment space is further defined between the first light shield, the at least one first light seal, the at least one second light seal, and the object.

In certain implementations of the system, the light shield is a first light shield. The system further includes a second robot, a second light shield coupled to the second robot, and at least one second light seal coupled to and co-movable with the second light shield. The second robot is configured to move the second light shield relative to the object, independently of movement of the first light shield by the first robot, to position the at least one second light seal in contact with the object and to further define the light containment space between first light shield, the at least one first light seal, the second light shield, the at least one second light seal, and the object.

In yet another method, a method of non-destructively inspecting an object includes forming a light containment space adjacent an object and generating a laser light within the light containment space for transmitting into the object. The method also includes, while keeping the object stationary, one of co-moving the light containment space and the laser light relative to the object, or moving the laser light relative to the object and the light containment space.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which:

FIG. 7 FIG. 5 is a cross-sectional side elevation view of the apparatus of FIG. 4, taken along the line 5-5 of FIG. 4, engaged with one side of the object and showing a light barrier engaged with an opposing side of the object.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Figure 1:
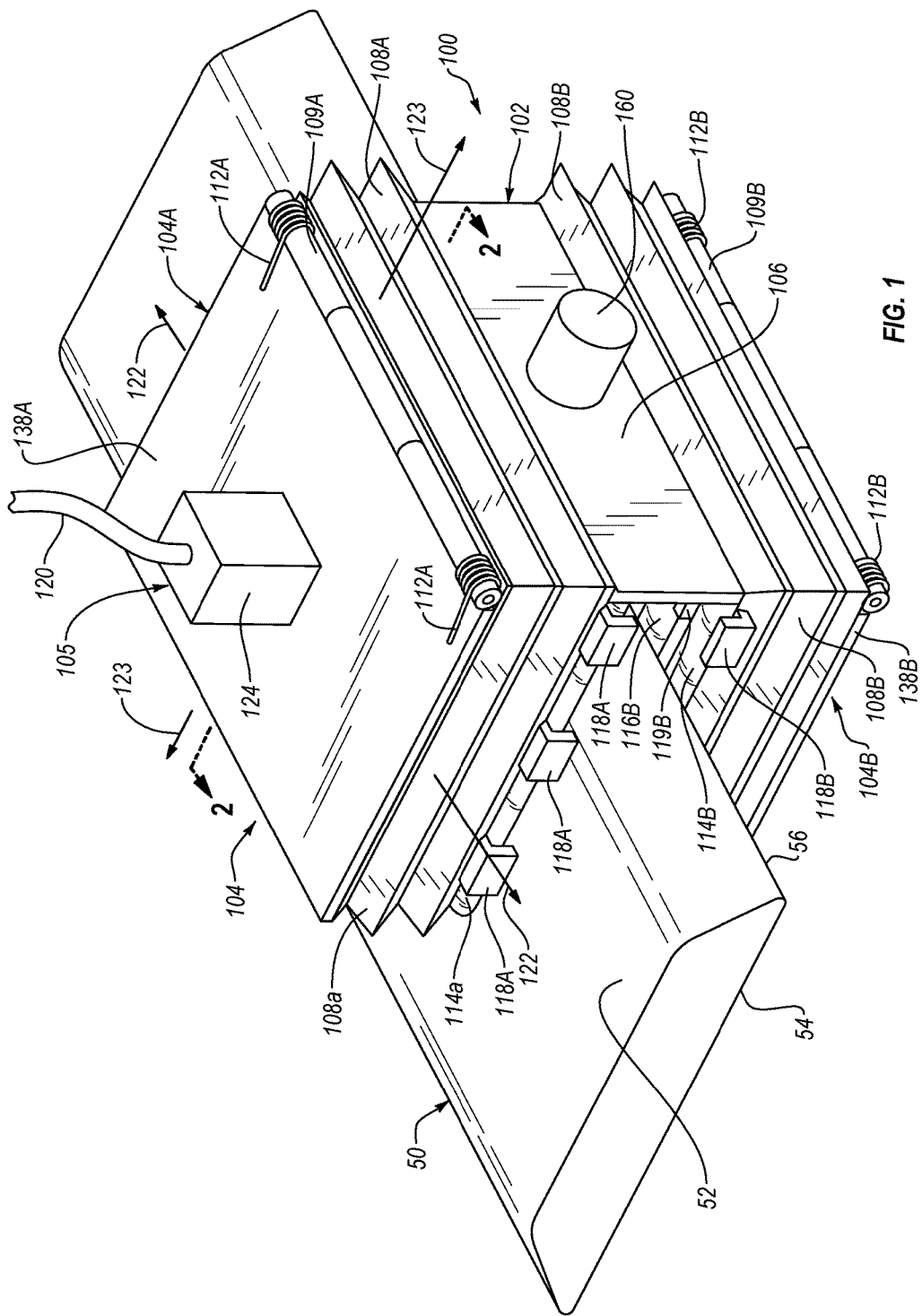
FIG. 1 is a perspective view of an apparatus for shielding light generated during the non-destructive inspection of an object, according to one or more embodiments of the present disclosure.
Figure 2:
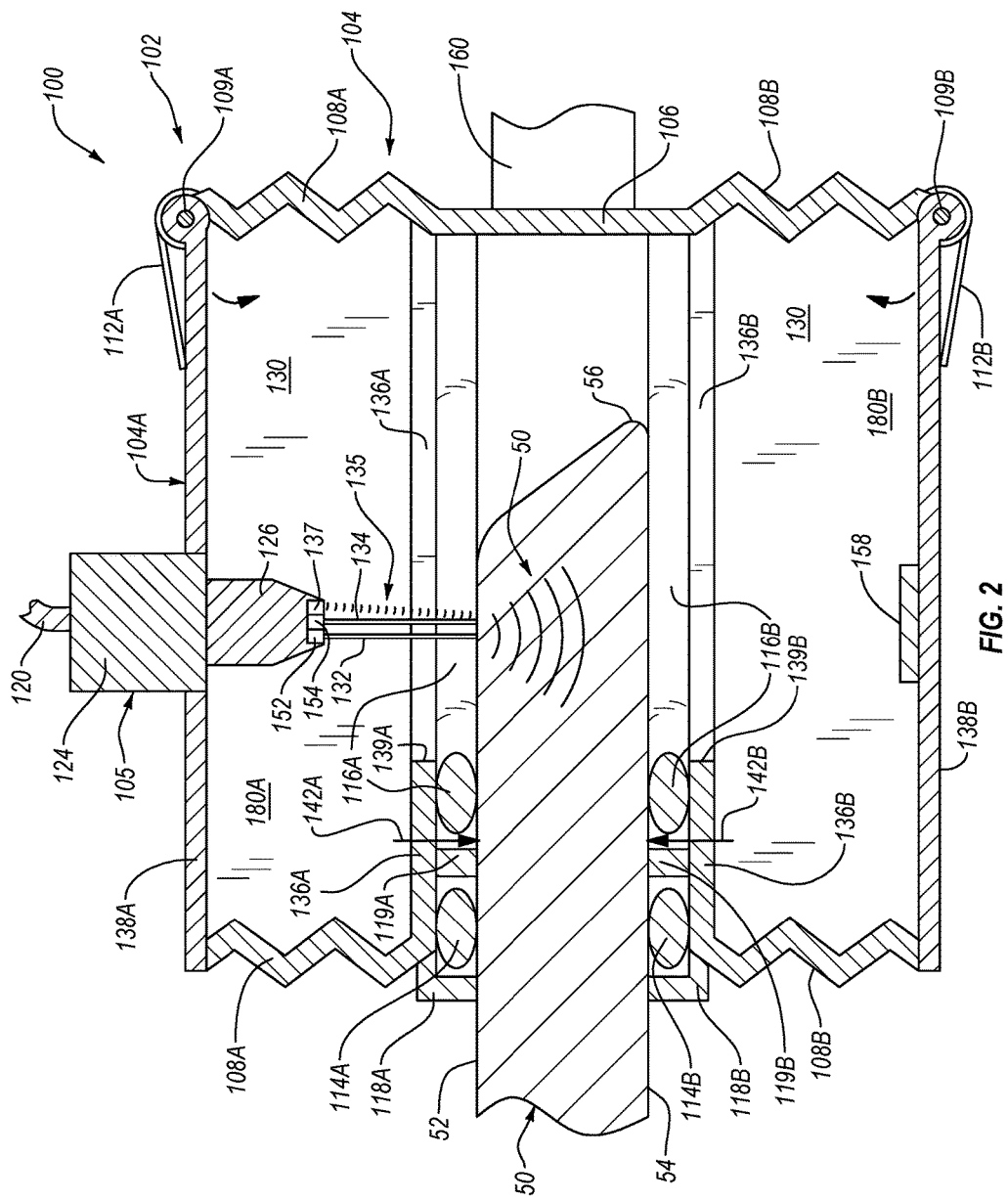
FIG. 2 is a cross-sectional side elevation view of the apparatus of FIG. 1 taken along the line 2-2 of FIG. 1, according to one or more embodiments of the present disclosure.

Referring to FIGS. 1 and 2, according to one embodiment, a system 100 for non-destructively inspecting an object 50, such as an external or non-enclosed edge portion along an edge 56 of the object, includes a robot 160 and an apparatus 102. In some implementations, as an example, the object 50 is a part of a larger structure, such as an aircraft, vehicle, building, bridge, spacecraft, and the like. The robot 160 is coupled to the apparatus 102 and controls movement of the apparatus 102 relative to the object 50. Although not shown, a controller controls movement of the robot 160 by sending commands to the robot 160. In response to the commands from the controller, the robot 160 moves accordingly, which in turn moves the apparatus 102 coupled to the robot 160. In this manner, the controller is configured, via operation of the robot 160, to position the apparatus 102 in a desired position, or move the apparatus 102 in a desired manner, relative to the object 50 for non-destructively inspecting the object 50, as will be described in more detail below. The robot 160 can be any of various robotic arms known in the art, such as mechanical arms with any of various links and components that cooperatively promote substantially unlimited linear and/or rotational movement of an end effector coupled to the robot. Generally, the apparatus 102 can be considered an end effector coupled to the robot 160.

The apparatus 102 includes a shield 104 and an inspection assembly 105. Generally, the inspection assembly 105 is configured to provide the physical interactions with the object 50 to non-destructively inspect the object 50. According to one embodiment, the inspection assembly 105 includes a shield interface 124 configured to engage and be mounted to the light shield 104. The inspection assembly 105 further includes a laser inspection head 126 coupled to the inspection assembly 105. In some implementations, when mounted to the light shield 104, the light shield interface 124 positions the laser inspection head 126 within a light containment space 130 at least partially defined by the light shield 104. The laser inspection head 126 includes a generation laser 152, a detection laser 154, and a light detector 137. The generation laser 152, which can be a Class-4 laser, generates a generation laser light beam 132, the detection laser 154 generates a detection laser light beam 134, and the light detector 137 receives and detects a reflected laser light beam 135, which is the detection laser light beam 134 after being reflected off of the surface of the object 50. Signals, such as command signals, power signals, and measurement signals, for operation of the generation laser 152, detection laser 154, and light detector 137 can be transmitted through the signal transmission line 120 or cable.

Generally, non-destructive inspection of the object 50 is performed by directing the generation laser light beam 132, from the generation laser 152, onto the surface (e.g., a first surface 53) of the object 50. The generation laser light beam 132 may be defined as short pulses of high energy laser light. The generation laser light beam 132 is absorbed into the object 50 to create localized heating of the object 50, the energy of which acts to expand the material of the object 50. The expansion of the material induces a stress wave 150 or ultrasonic wave that propagates through the object 50, causing the surface of the object 50 to vibrate. The vibrations of the surface of the object 50 change the wavelength of the detection laser light beam 134 as it reflects off of or scatters from the surface of the object 50 as the reflected laser light beam 135. The reflected laser light beam 135 is then received and detected by the light detector 137, which converts the reflected laser light beam 135 into a carrier signal. Although not shown, a controller or computing module may include an interferometer, or other similar device, configured to determine an ultrasonic signal, representative of the ultrasonic wave 150 passing through the object 50, based on the carrier signal. Generally, from the characteristics of the ultrasonic signal, the structural health of the object 50, in terms of structural defects (e.g., delaminations, inclusions, voids, disbands, and porosity) in the object 50, can be determined. Furthermore, to non-destructively inspect an area of the object 50, the inspection assembly 105 is moved along the object 50 while generating the generation laser light beam 132 and the detection laser light beam 134.

As shown in FIGS. 1 and 2, in some embodiments, the inspection assembly 105 is non-movably fixed relative to the light shield 104. Accordingly, in order to move the inspection assembly 105 relative to the object 50, the light shield 104 also moves relative to the object 50, which in turn moves the light containment space 130 relative to the object 50. The light shield 104 has a generally clam-shape design, with a first portion 104A spaced apart from a second portion 104B by a spine 106, to effectively wrap around the edge 56 of the object 50. In some implementations, the first portion 104A includes some features matching the second portion 104B, such that the first portion 104A is substantially a mirror image of the second portion 104B. The first and second portions 104A, 104B of the light shield 104 include respective closed ends 138A, 138B, sidewalls 108A, 108B, and openings 139A, 139B or open ends that oppose the close ends. The respective sidewalls 108A, 108B extend (e.g., transversely) from respective closed ends 138A, 138B and collectively define the openings 139A, 139B. Each of the first and second portions 104A, 104B of the light shield 104 includes a respective one of spaces 180A, 180B defined between respective sidewalls 108A, 108B, closed ends 138A, 138B, and openings 139A, 139B. The spaces 180A, 180B define respective portions of the light containment space 130 of the apparatus 102.

The first and second portions 104A, 104B are configured to define respective spaces 180A, 180B having any of various shapes and sizes. In some implementations, the space 180A defined by the first portion 104A is the same as the space 180B defined by the second portion 104B. However, in other implementations, the space 180A defined by the first portion 104A is different (e.g., has a different size, shape, etc.) than the space 180B defined by the second portion 104B. According to the illustrated implementation, the respective spaces 180A, 180B of the first and second portions 104A, 104B have a substantially square or rectangular cross-sectional shape along a plane parallel to the inspection direction 122 (i.e., the direction the laser inspection head 126 moves during inspection of the object 50). In the illustrated implementation, the first and second portions 104A, 104B each has four respective sidewalls 108A, 108B and the closed ends 138A, 138B and the openings 139A, 139B are square or rectangular shaped. In other implementations, the spaces 180A, 180B can have any of various cross-sectional shapes, the first and second portions 104A, 104B can each have fewer or more than four sidewalls 108A, 108B, and the closed ends 138A, 138B and the openings 139A, 139B can have any of various shapes.

The sidewalls 108A, 108B and closed ends 138A, 138B of the light shield 104 are each made of an opaque material formed to have a generally thin-walled construction. The opaque material can be any of various opaque materials known in the art. Moreover, although shown as having a single layer of material in the illustrated embodiment, each of the sidewalls 108A, 108B and closed ends 138A, 138B can have multiple layers of materials. The sidewalls 108A, 108B and closed ends 138A, 138B of the light shield 104 are at least semi-rigid (e.g., rigid enough to maintain the shape of the spaces 180A, 180B under normal atmospheric pressure). According to one embodiment, one or more of the sidewalls 108A, 108B and closed ends 138A, 138B of the light shield 104 includes a rigid frame to which a relatively flexible opaque sheet is attached (see, e.g., the light shield 204 of FIG. 5).

Figure 3:
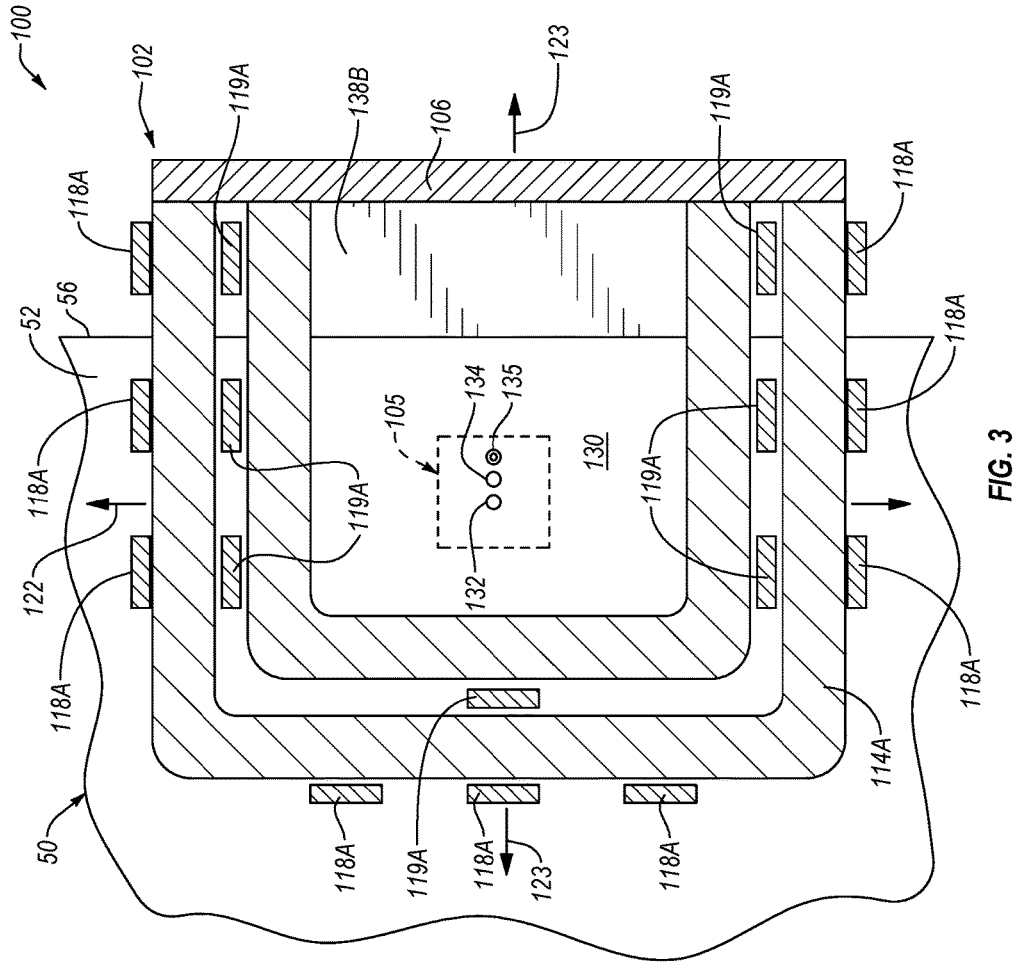
FIG. 3 is a cross-sectional side elevation view of the apparatus of FIG. 1 taken along the line 3-3 of FIG. 2, according to one or more embodiments of the present disclosure.

Still referring to FIGS. 1 and 2, and also referring to FIG. 3, the apparatus 102 further includes at least one light seal coupled to respective first and second portions 104A, 104B of the light shield 104. More specifically, the light seals are coupled to respective sidewalls 108A, 108B of the first and second portions 104A, 104B. For example, according to the illustrated embodiment, the first portion 104A includes a first outer light seal 114A and a first inner light seal 116A both fixed to the sidewalls 108A and at least partially extending about (e.g., encompassing or encircling) the opening 139A. Similarly, in the illustrated embodiment, the second portion 104B includes a second outer light seal 114B and a second inner light seal 116B both fixed to the sidewalls 108B and at least partially extending about (e.g., encompassing or encircling) the opening 139B. As shown in FIG. 3, each light seal may encompass three sides of the shield 104 and abut up against the spine 106.

Although respective inner and outer light seals are shown spaced apart from each other in a direction parallel to the inspection direction 122, in other implementations, respective inner and outer light seals may abut each other. Furthermore, although in the illustrated embodiments, two light seals are fixed to each of the first and second portions 104A, 104B of the light shield 104 for redundancy or to improve the light containment performance of the apparatus 102, in other embodiments, only one light seal or more than two light seals are fixed to each of the first and second portions 104A, 104B of the light shield 104.

Each of the first and second outer light seals 114A, 114B and the first and second inner light seals 116A, 116B can have any of various shapes and be made from any of various materials that are configured to block the transmission of light. Generally, the lights seals are resiliently flexible and opaque. Resilient flexibility of the light seals facilitates a secure light barrier between the object 50 and the light shield 104 to prevent light from passing between the object 50 and the light shield 104. For example, the light seals can resiliently flex or deform against the surface of the object 50 to form a light leak-proof seal with the object 50. Moreover, the light seals can be made from, or include, friction-reducing materials that promote movement of the light seals along (e.g., sliding or gliding on) the object 50 while in contact with the object 50. For example, in one implementation, each light seal is made from a brush that includes a plurality of tightly-packed bristles. According to another implementation, for example, each light seal includes an elongate strip of foam. In yet another implementation, for example, each light seal includes a strip of rubber, or other material, coated with a low-friction material, such as Teflon®.

The first and second outer light seals 114A, 114B and the first and second inner light seals 116A, 116B are coupled to the respective sidewalls 108A, 108B of the light shield 104. In some embodiments, the sidewalls 108A, 108B include respective platforms 136A, 136B to which the light seals can be coupled. The platforms 136A, 136B extend about and define the openings 139A, 139B of the respective first and second portions 104A, 104B of the light shield 104. The first and second outer light seals 114A, 114B and the first and second inner light seals 116A, 116B can be coupled to the respective platforms 136A, 136B using any of various coupling techniques known in the art, such as fastening techniques, adhesion techniques, bonding techniques, or the like.

The apparatus 102 further includes at least one biasing mechanism configured to urge resilient deformation of the first and second outer light seals 114A, 114B and the first and second inner light seals 116A, 116B against the object 50 when the object 50 is positioned between the first and second portions 104A, 104B of the light shield 104. Although the at least one biasing mechanism can be any of various biasing mechanisms known in the art, in some embodiments, the at least one biasing mechanism is one or more of at least one concertinaed sidewall of the light shield and at least one spring. In other words, although in the illustrated embodiments, the at least one biasing mechanism of the apparatus 102 includes both concertinaed sidewalls 108A, 108B and springs 112A, 112B, in some embodiments, the apparatus 102 includes only one of concertinaed sidewalls 108A, 108B or springs 112A, 112B.

The concertinaed sidewalls 108A, 108B of the apparatus 102 collectively form a bellows, which facilitates biased movement of the first and second outer light seals 114A, 114B and the first and second inner light seals 116A, 116B relative to the closed ends 138A, 138B, respectively, in an accordion-like manner. As shown in FIG. 2, the concertinaed configuration of the sidewalls 108A, 108B impart a bias to the first and second outer light seals 114A, 114B and the first and second inner light seals 116A, 116B in respective directions 142A, 142B away from the closed ends 138A, 138B. Accordingly, when the apparatus 102 is moved into position relative to the object 50, such that the first and second outer light seals 114A, 114B contact the first surface 52 of the object 50, and the first and second inner light seals 116A, 116B contact the second surface 54 of the object 50, the concertinaed sidewalls 108A, 108B urge the respective light seals against the first and second surfaces 52, 54 to resiliently deform the light seals against the first and second surfaces 52, 54.

In some embodiments, the closed ends 138A, 138B and the sidewalls 108A, 108B to which the light seals are coupled are movable (e.g., pivotable) relative to the spine 106 about respective hinges 109A, 109B. The hinges 109A, 109B can each be a rod that defines an axis-of-rotation about which the respective closed ends 138A, 138B and sidewalls 108A, 108B pivot. The springs 112A, 112B, which can be torsional springs, are coupled to the hinges 109A, 109B and engaged with the closed ends 138A, 138B to rotationally or pivotally bias the closed ends 138A, 138B, and thus the sidewalls 108A, 108B and light seals 114A, 114B, 116A, 116B, in the rotational directions 140A, 140B, respectively, about the hinges 109A, 109B and toward the object 50.

Although not shown, in some implementations, the light shield 104 includes a flexible or movable screen enclosing or covering a space immediately adjacent the spine 106 and between the light seals of opposing first and second portions 104A, 104B of the light shield 104. Normally, light would not exit this space. However, under certain unique circumstances, if light is prone to exiting this space, the screen is configured to block such light. The screen can be a sliding screen or spring-loaded screen that engages the edge 56 of the object 50. Alternatively, or additionally, the light seals may be four-sided (e.g., square or rectangle shaped), to enclose a space between the four sides, and configured such that all four sides engage and form a light seal against the first and second surfaces 52, 54.

The apparatus 102 includes at least one light sensor positioned to detect light at a location constrained from light by at least one of the first and second outer light seals 114A, 114B, the first and second inner light seals 116A, 116B, and the object 50. Generally, the at least one light sensor is configured to detect light that has unintentionally escaped the light containment space 130.

In some embodiments, the apparatus 102 includes multiple outer light sensors 118A, 118B positioned external to respective outer light seals 114A, 114B. In other words, the outer light sensors 118A, 118B are positioned such that respective outer light seals 114A, 114B are positioned between respective outer light sensors 118A, 118B and respective openings 139A, 139B. According to implementations with both outer light seals 114A, 114B and inner light seals 116A, 116B, the outer light sensors 118A, 118B are positioned such that respective outer light seals 114A, 114B are positioned between respective outer light sensors 118A, 118B and respective inner light seals 116A, 116B. In this manner, the outer light sensors 118A, 118B are positioned to detect light escaping from the light containment space 130 through or around the outer light seals 114A, 114B. Referring to FIG. 3, in certain implementations, the apparatus 102 can include multiple outer light sensors 118A, 118B spaced apart on each side, other than or including the side coextensive with the spine 106, of the apparatus 102. However, in other implementations, the apparatus 102 may include single outer light sensors 118A, 118B each detecting light from all sides of the apparatus 102, excluding or including the side coextensive with the spine 106, or single outer light sensors 118A, 118B on each side of the apparatus 102, excluding or including the side coextensive with the spine 106.

Similar to the outer light sensors 118A, 118B, in some embodiments, for example, the apparatus 102 includes multiple inner light sensors 119A, 119B positioned internal to respective outer light seals 114A, 114B and external to respective inner light seals 116A, 116B. In other words, the inner light sensors 119A, 119B are positioned such that respective inner light seals 116A, 116B are positioned between respective inner light sensors 119A, 119B and respective openings 139A, 139B. According to implementations with both outer light seals 114A, 114B and inner light seals 116A, 116B, the inner light sensors 118A, 118B are positioned between respective outer light seals 114A, 114B and respective inner light seals 116A, 116B. In this manner, the inner light sensors 119A, 119B are positioned to detect light escaping from the light containment space 130 through or around the inner light seals 116A, 116B. Referring to FIG. 3, in certain implementations, the apparatus 102 can include multiple inner light sensors 119A, 119B spaced apart on each side, other than or including the side coextensive with the spine 106, of the respective openings 139A, 139B. However, in other implementations, the apparatus 102 may include single inner light sensors 119A, 119B each detecting escaping light from all sides of the respective openings 139A, 139B, excluding or including the side coextensive with the spine 106, or single inner light sensors 119A, 119B on each side of respective openings 139A, 139B, excluding or including the side coextensive with the spine 106.

Referring to FIG. 2, the apparatus 102 may also include a light sensor 158 configured to detect light and positioned to receive the generation laser light beam 134 when the path of the generation laser light beam 134 is unobstructed by the object 50. In other words, the light sensor 158 is aligned with the path of the generation laser light beam 134. In one implementation, with the inspection assembly 105 fixed to, or at least fixed relative to, the first portion 104A of the light shield 104, the light sensor 158 is fixed to, or at least fixed relative to, the second portion 104B of the light shield 104. More specifically, the light sensor 158 is positioned within the light containment space 130 of the apparatus 102 at a location spaced apart from the generation laser 152 by a distance greater than a thickness of the object 50 to be inspected.

The light sensors of the apparatus 102 may be coupled to a controller (not shown) that is configured to control operations of the apparatus 102 based, at least in part, on signals received from the light sensors. For example, in some implementations, the controller is configured to disable or turn-off at least the generation laser 152 if a threshold level of light is detected by any one or more of the outer and/or inner light sensors 118A, 118B, 119A, 119B indicating a threshold level of light is escaping the light containment space 130. Similarly, the controller may be configured to disable or turn-off at least the generation laser 152 if a threshold level of light is detected by the light sensor 158 indicating the generation laser light beam 132 is missing or not being absorbed by the object 50. Alternatively, or additionally, the controller may be configured to enable inspection operations of the apparatus 102 if a threshold level of light is not detected by the light sensor 158 indicating the generation laser light beam 132 is contacting or being absorbed by the object 50.

Additionally, the apparatus 102 includes one or more interlock switches in some embodiments. The interlock switches are configured to detect proper placement of the apparatus 102 about the object 50 to be inspected. For example, the interlock switch can be positioned on one or both of the first and second portions 104A, 104B of the shield 104 and be configured to detect engagement with respective sides of the object 50 when the apparatus 102 is properly positioned about the object 50. Generally, the controller can be configured to disable (e.g., prevent from turning on) operation of the apparatus 102, including the generation laser 152, when the interlock switches detect improper positioning of the apparatus 102 about the object 50 or do not detect proper positioning of the apparatus 102 about the object 50. In contrast, the controller can be configured to enable (e.g., allow turning on) operation of the apparatus 102, including the generation laser 152, only when the interlock switches detect proper positioning of the apparatus 102 about the object 50 (e.g., engage respective sides of the object 50).

As defined herein, the controller, or control module, is operably coupled with the apparatus 102, such as via the robot 160, to numerically control operation of the apparatus 102. For example, the controller may include programmable logic that causes commands and power to be transmitted to the apparatus 102 to control the operating characteristics of the apparatus 102. Additionally, the controller may be configured to numerically control movement of the apparatus 102 relative to the object 50 via the robot 160.

The object 50 can be made from any of various materials, such as metals, plastics, fiber-reinforced composites, and the like. Moreover, the object 50 can include a single layer of material or multiple layers of the same or different materials.

Figure 4:
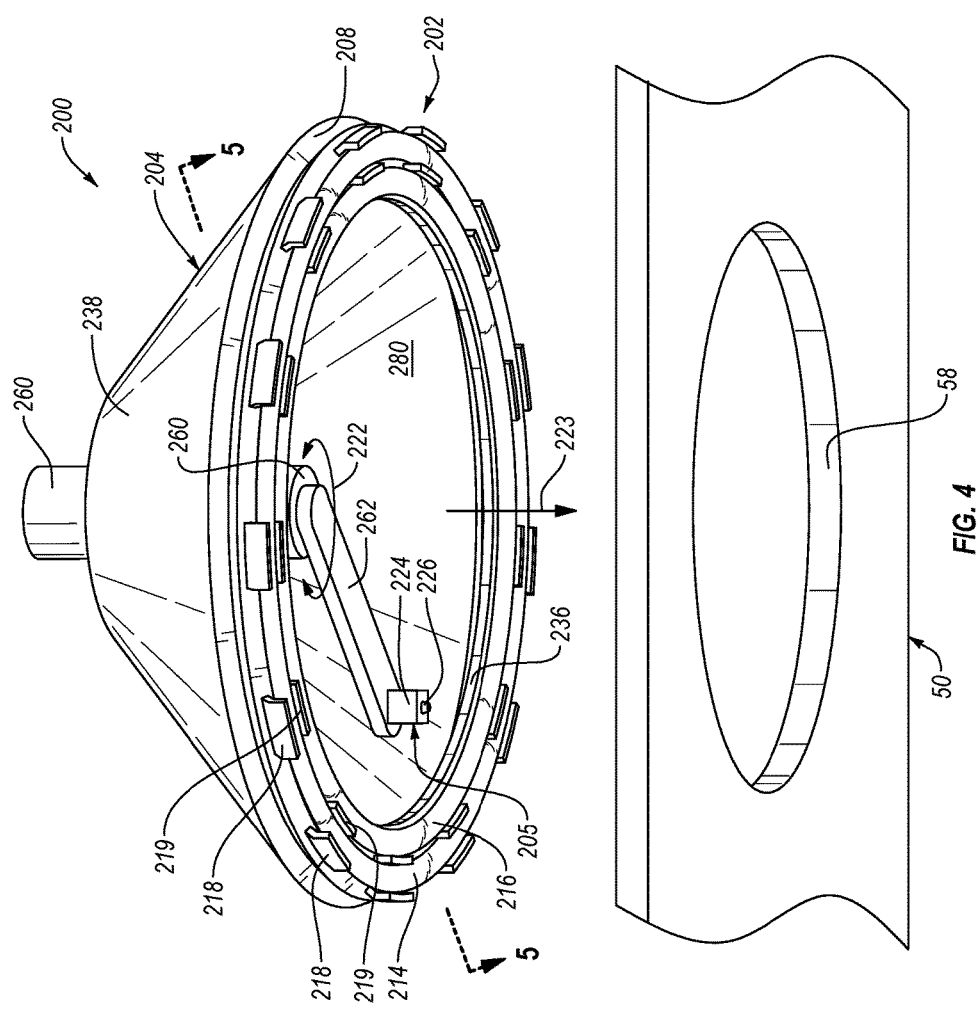
FIG. 4 is perspective view of an apparatus for shielding light generated during the non-destructive inspection of an object, according to one or more other embodiments of the present disclosure.
Figure 5:
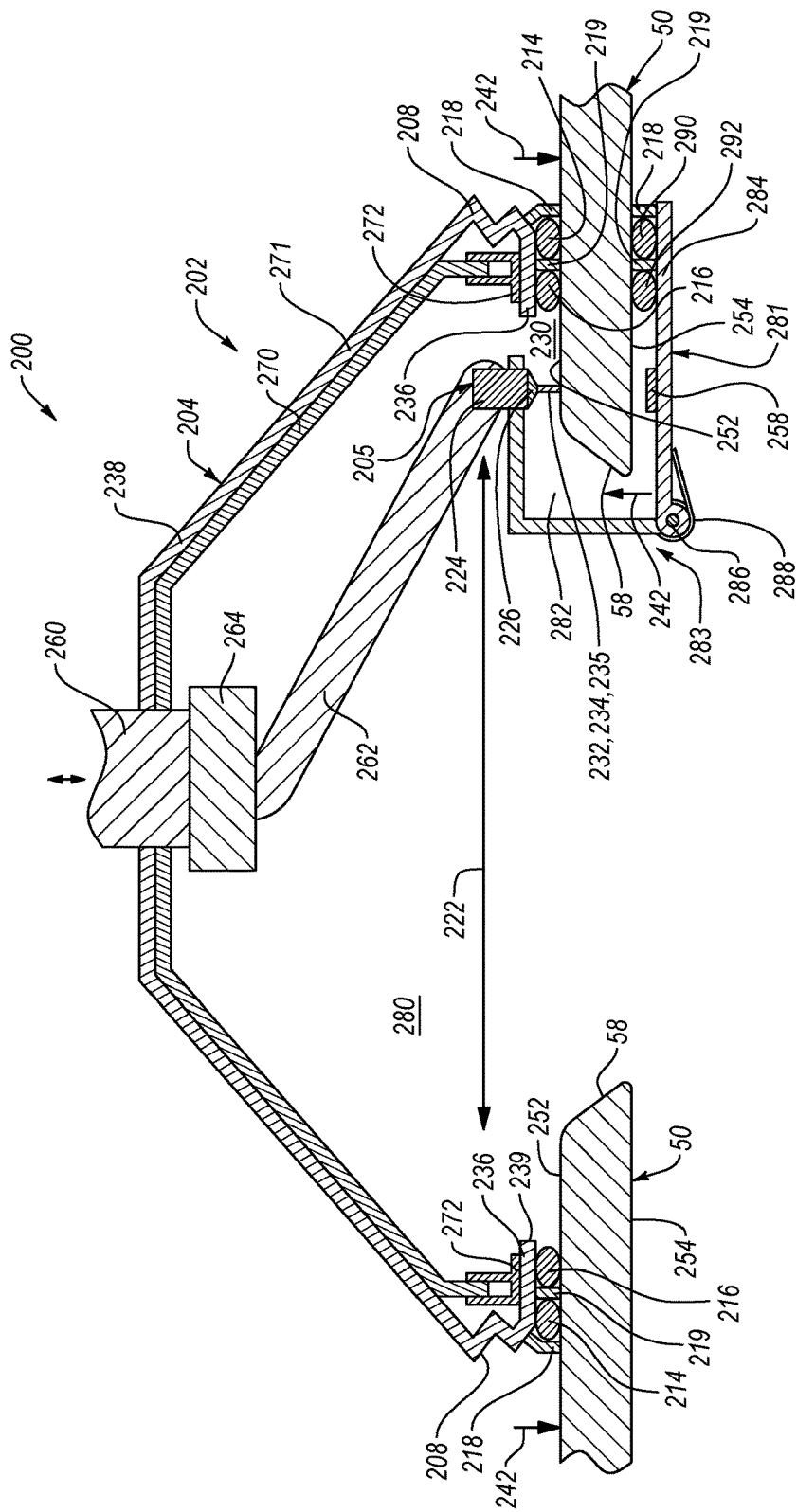
FIG. 5 is a cross-sectional side elevation view of the apparatus of FIG. 4, taken along the line 5-5 of FIG. 4, engaged with the object and including a light shield module, according to one or more embodiments of the present disclosure.

Referring now to FIGS. 4 and 5, according to one embodiment, a system 200 for non-destructively inspecting an object 50, such as an internal or enclosed edge portion of a hole 58 in the object 50, includes a robot 260 and an apparatus 202. The robot 260 is coupled to the apparatus 202 and controls movement of the apparatus 202 relative to the object 50. Although not shown, a controller controls movement of the robot 260 by sending commands to the robot 260. In response to the commands from the controller, the robot 260 moves accordingly, which in turn moves the apparatus 202 coupled to the robot 260. In this manner, the controller is configured, via operation of the robot 260, to position the apparatus 202 in a desired position, or move the apparatus 202 in a desired manner, relative to the object 50 for non-destructively inspecting the object 50, as will be described in more detail below. The robot 260 can be similar to the robot 160 of FIGS. 1-3. Generally, the apparatus 202 can be considered an end effector coupled to the robot 260.

Like the apparatus 102 of FIGS. 1-3, the apparatus 202 includes a shield 204 and an inspection assembly 205. However, instead of being non-movably fixed to the light shield 204, as with the inspection assembly 105 of the apparatus 102, the inspection assembly 205 is movably fixed to the light shield 204 via an arm 262. The arm 262 is movable via an actuation mechanism 264 coupled to the robot 260. In one implementation, the arm 262 is movable in a rotational direction 222 about the hole 58 formed in the object 50. The actuation mechanism 264 is controlled by a controller directly or via the robot 260 to move the arm 262 relative to the light shield 204 and the object 50 during inspection of the object 50.

Like the inspection assembly 105, the inspection assembly 205 is configured to provide the physical interactions with the object 50 necessary to non-destructively inspect the object 50. The inspection assembly 205 is fixed to an end portion of the arm 262 and thus moves with the arm 262. According to one embodiment, the inspection assembly 205 includes an arm interface 224 configured to engage and be mounted to the arm 262. In one implementation, the arm interface 224 facilitates adjustment of the position of the inspection assembly 205 relative to the arm 262. The inspection assembly 205 further includes a laser inspection head 226 coupled to the inspection assembly 205. When mounted to the arm 262, the light shield interface 224 positions the laser inspection head 226 within a light containment space 230 at least partially defined by the light shield 204 and a light shield module 281 fixed relative to the laser inspection head 226. Although not shown in detail, the laser inspection head 226 includes a generation laser, detection laser, and light detector similar to or the same as the generation laser 152, the detection laser 154, and the light detector 137 of the laser inspection head 126. Accordingly, the laser inspection head 226 can generates a generation laser light beam 232, a detection laser light beam 234, and a reflected laser light beam 235, shown collectively in FIG. 5.

During inspection of the object 50 by the inspection assembly 205, the light shield 204 is stationary relative to the object 50. Generally, the light shield 204 is configured to cover and seal the entirety of the hole 58 on a first side 52 of the object 50. Accordingly, the light shield 204 can have any of various shapes sized to sufficiently cover the hole 58. In the illustrated embodiment, the light shield 204 has a generally conical shape that diverges in a direction from the robot 260 to the sidewall 208. However, in other embodiments, the light shield 204 can have a cylindrical shape or even a polygonal shape. The light shield 204 includes a closed end 238, a sidewall 208, and an opening 239 or open end. The sidewall 208 extends from the closed end 238 and defines the opening 239. The light shield 104 includes a space 280 defined between the sidewall 208, closed end 238, and opening 239. The space 280 defines a portion of the light containment space 230 of the apparatus 202.

The sidewall 208 and closed end 238 of the light shield 204 are each made of an opaque material formed to have a generally thin-walled construction. The opaque material can be any of various opaque materials known in the art. According to one embodiment, the sidewall 208 and closed end 238 of the light shield 204 includes a rigid frame 270 to which a relatively flexible opaque sheet 271 is attached. Although shown as having multiple layers (e.g. a frame 270 and sheet 271), in some embodiments, the light shield 204 may have a single layer of material.

The apparatus 202 further includes at least one light seal coupled to the light shield 204. More specifically, the light seals are coupled to the sidewall 208 of the light shield 204. For example, according to the illustrated embodiment, the light shield 204 includes a first outer light seal 214 and a first inner light seal 216 both fixed to the sidewall 208 and at least partially extending about (e.g., encompassing or encircling) the opening 239. As shown in FIG. 4, the first outer and inner light seals 214, 216 have a generally annular shape that corresponds with the circular shape of the hole 58 in the object 50. Although the first inner and first outer light seals are shown spaced apart from each other in a direction parallel to the rotational direction 222, in other implementations, the inner and outer light seals may abut each other. Furthermore, although in the illustrated embodiments, two light seals are fixed to the light shield 204 for redundancy or to improve the light containment performance of the apparatus 202, in other embodiments, only one light seal or more than two light seals are fixed to the light shield 204.

Like the first and second outer light seals 114A, 114B and the first and second inner light seals 116A, 116B of the apparatus 102, each of the first outer light seal 214 and the first inner light seal 216 can have any of various shapes and be made from any of various materials that are configured to block the transmission of light. Accordingly, the first outer light seal 214 and the first inner light seal 216 can be configured in a manner similar to the first and second outer light seals 114A, 114B and the first and second inner light seals 116A, 116B, as described above.

The first outer and inner light seals 114, 116 are coupled to the sidewall 208 of the light shield 204. In some embodiments, the sidewall 208 includes a platform 236 to which the light seals can be coupled. The platform 236 extends about and defines the opening 239 of the light shield 204. Accordingly, the platform 236 has a generally annular shape. The first outer and inner light seals 114, 116 can be coupled to the platform 236 using any of various coupling techniques known in the art, such as fastening techniques, adhesion techniques, bonding techniques, or the like.

The apparatus 202 further includes at least one biasing mechanism configured to urge resilient deformation of the first outer and inner light seals 214, 216 against the object 50 when the object 50 is being inspected. Although the at least one biasing mechanism can be any of various biasing mechanisms known in the art, in some embodiments, the at least one biasing mechanism is a concertinaed sidewall 208 of the light shield 204. Like the concertinaed sidewalls 108A, 108B of the apparatus 102, the concertinaed sidewall 208 forms a bellows, which facilitates biased movement of the first outer and inner light seals 214, 216 relative to the closed end 238 of the light shield 204 in an accordion-like manner. As shown in FIG. 5, the concertinaed configuration of the sidewall 208 imparts a bias to the first outer and inner light seals 214, 216 in a direction 242 away from the closed end 238. Accordingly, when the light shield 204 is moved into position relative to the object 50, such that the first outer and inner light seals 214, 216 contact the first surface 52 of the object 50, the concertinaed sidewall 208 urges the light seals against the first surface 52 to resiliently deform the light seals against the first surface 52.

To facilitate the flex of the concertinaed sidewall 208, and allow biased movement of the first outer and inner light seals 214, 216 relative to the closed end 238, the rigid frame 270 may be allowed to move relative to the first outer and inner light seals 214, 216 via engagement with a slotted bracket 272 coupled to the light shield 204. The slotted bracket 272 includes a slot that retains an open end of the frame 270 while allowing the open end to move parallel to the direction 242.

As shown in FIG. 5, the apparatus 102 further includes the light shield module 281. Generally, the light shield module 281 is configured to facilitate a light seal with the second surface 54 of the object 50 while moving relative to the object 50. The light shield module 281 defines a space 282 that, together with the space 280 defined by the light shield 204, forms the light containment space 230, which is movable relative to the object 50 as the light shield module 281 moves relative to the object. According to the illustrated embodiment, the light shield module 281 includes a bracket 283 designed to wrap around only a portion of the edge of the object defining the hole 58. Therefore, the bracket 283 has a substantially U-shaped cross section. The bracket 283 is fixedly coupled directly to the arm 262 or the inspection assembly 205, and thus moves with the inspection assembly 205.

The bracket 283 further includes at least one light seal coupled to a portion 284 (e.g., panel) of the bracket 283 directly adjacent the second surface 54 of the object 50 during inspection of the object 50. According to the illustrated embodiment, the bracket 283 includes a second outer light seal 290 and a second inner light seal 292 both fixed to the portion 284 of the bracket 283 and at least partially extending about (e.g., encompassing or encircling) the portion 284. The second outer and inner light seals 290, 292 may each have a generally annular shape or a non-continuous shape, such as a semi-circular or U-shape. Although the second inner and outer light seals 290, 292 are shown spaced apart from each other in a direction parallel to the rotational direction 222, in other implementations, the second inner and outer light seals may abut each other. Furthermore, although in the illustrated embodiments, two light seals are fixed to the portion 284 of the bracket 283 for redundancy or to improve the light containment performance of the apparatus 202, in other embodiments, only one light seal or more than two light seals are fixed to the portion 284.

Although not shown, in some implementations, as mentioned above with regard to the light shield 104, the light shield 204 may include a flexible or movable screen enclosing or covering a space immediately adjacent the bracket 283 and between opposing light seals of the light shield module 281. The screen can be a sliding screen or spring-loaded screen that engages the edge of the hole 58 of the object 50.

The apparatus 102 further includes at least one biasing mechanism configured to urge resilient deformation of the second outer and inner light seals 290, 292 against the object 50 when the bracket 283 is wrapped about the object 50. In some embodiments, the portion 284 of the bracket 283 is movable (e.g., pivotable) about a hinge 286. The hinge 286 can be a rod that defines an axis-of-rotation of the portion 284 relative to the rest of the bracket 283. The at least one biasing mechanism can be one or more springs 288, which can be torsional springs, coupled to the hinge 286 and engaged with the portion 284 of the bracket 283 to rotationally or pivotally bias the portion 284, and thus the light seals 290, 292, in the rotational direction 242 about the hinge 286 toward the object 50.

The apparatus 202 includes at least one light sensor positioned to detect light at a location constrained from light by at least one of the first outer and inner light seals 214, 216, the second outer and inner light seals 290, 292, and the object 50. Generally, the at least one light sensor is configured to detect light that has unintentionally escaped the light containment space 230. In some embodiments, the apparatus 202 includes one or multiple outer light sensors 218 positioned external to respective first and second outer light seals 214, 290. Additionally, in certain embodiments, the apparatus 202 can include one or multiple inner light sensors 219 positioned internal to respective first and second outer light seals 214, 290 and external to respective first and second inner light seals 216, 292. The apparatus 202 may also include a light sensor 258, similar to light sensor 158, configured to detect light and positioned to receive the generation laser light beam 134 when the path of the generation laser light beam 134 is unobstructed by the object 50.

Figure 6:
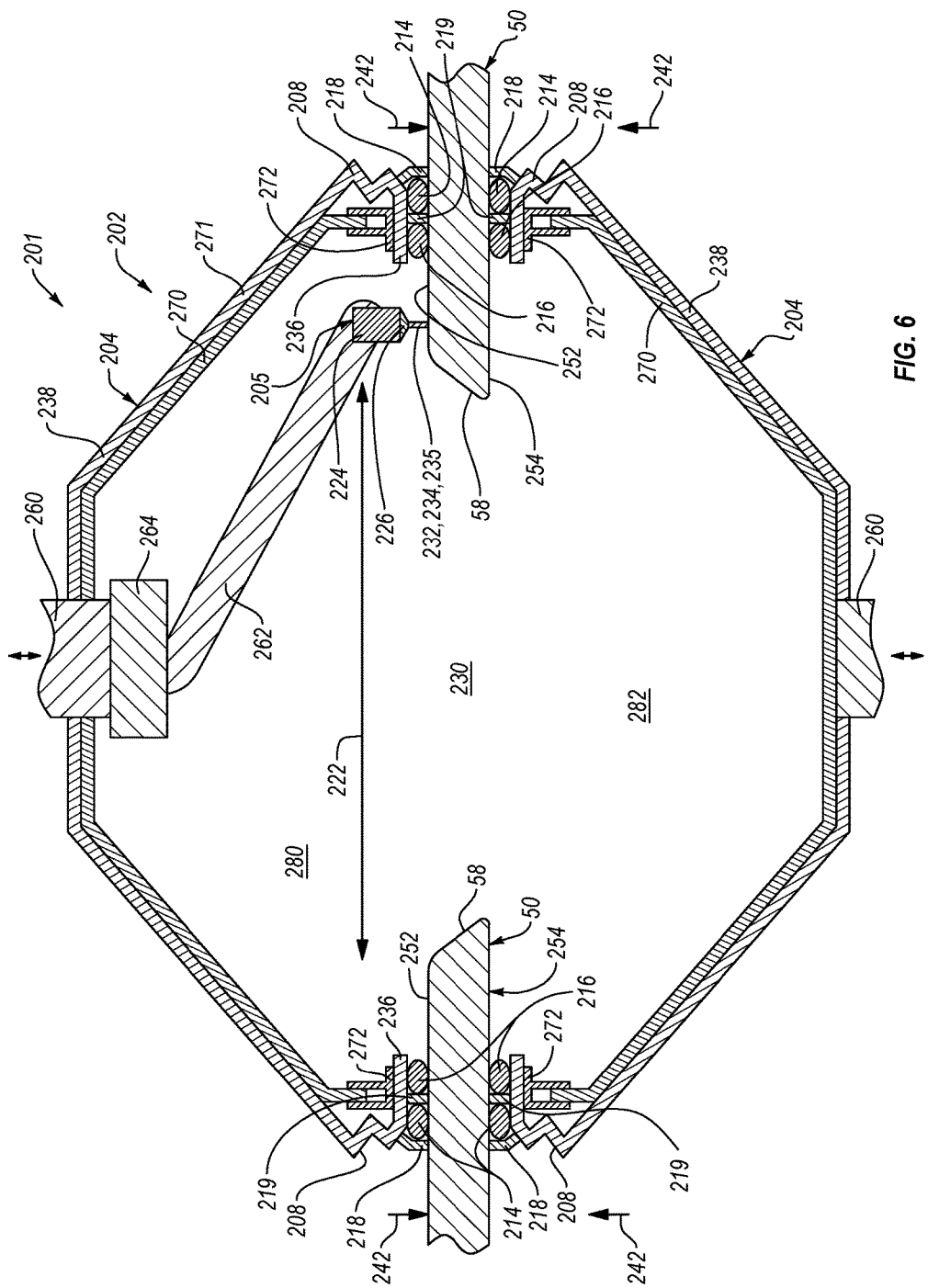
FIG. 6 is a cross-sectional side elevation view of the apparatus of FIG. 4, taken along the line 5-5 of FIG. 5, engaged with one side of the object and showing a second apparatus, for shielding light generated during the non-destructive inspection of an object, engaged with an opposing side of the object.

Referring to FIG. 6, according to one embodiment, a system 201 for non-destructively inspecting an object 50, such as an internal or enclosed edge portion of a hole 58 in the object 50, is shown. The system 201 is similar to the system 200 of FIGS. 4 and 5. However, instead of enclosing the light containment space 230 with a light shield module, the system 201 utilizes a second shield 207, and associated lights seals 216, 218, substantially identical to the light shield 204. The second shield 207 and light seals 216, 218 coupled to the second shield 207 is coupled to a second robot 261 that controls movement of the second shield 207 independently of the control of movement of the light shield 204 by the robot 260. The second shield 207 is moved into position relative to the object 50, such that the light seals of the second shield 207 contact the second surface 54 of the object 50. The concertinaed sidewall 208 of the second shield 207 urges the light seals of the second shield 207 against the second surface 54 to resiliently deform the light seals against the second surface 54. With the light seals of the light shield 204 resiliently deformed or in contact with the first surface 52 of the object 50 and the light seals of the second shield 207 resiliently deformed or in contact with the first surface 52 of the object, the light containment space 230, formed by the spaces 280, 282 defined by the light shields, is enclosed.

Figure 7:
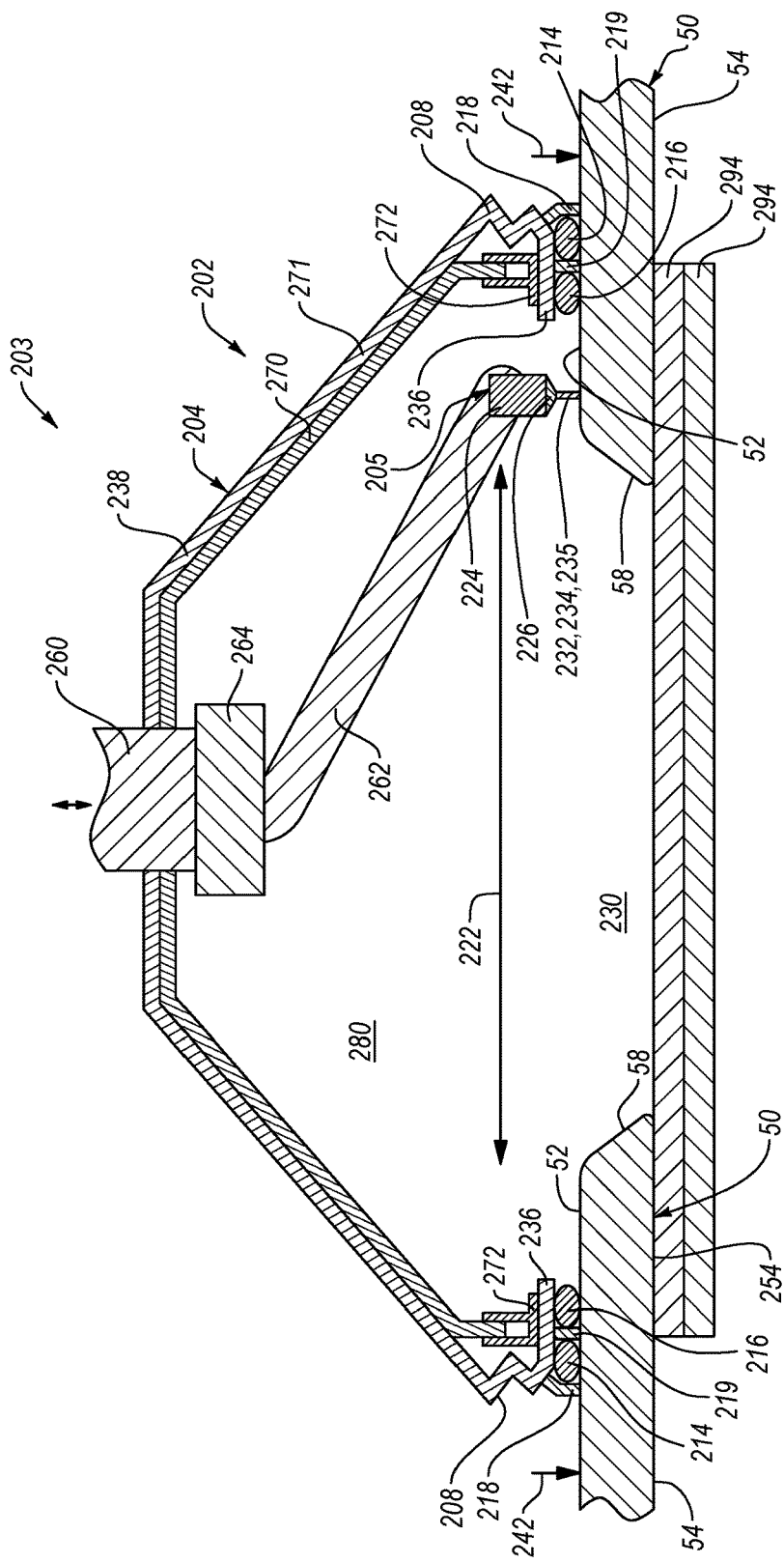

As shown in FIG. 7, according to another embodiment, a system 203 for non-destructively inspecting an object 50 is shown. The system 203 is similar to the system 201, except that the second shield 207 is replaced with an opaque barrier 294, which can be an opaque curtain or wall. In certain implementations, as shown, the system 203 may include multiple opaque barriers 294 adjacent each other for redundancy or to improve the light containment performance of the apparatus system 203.

Figure 8:
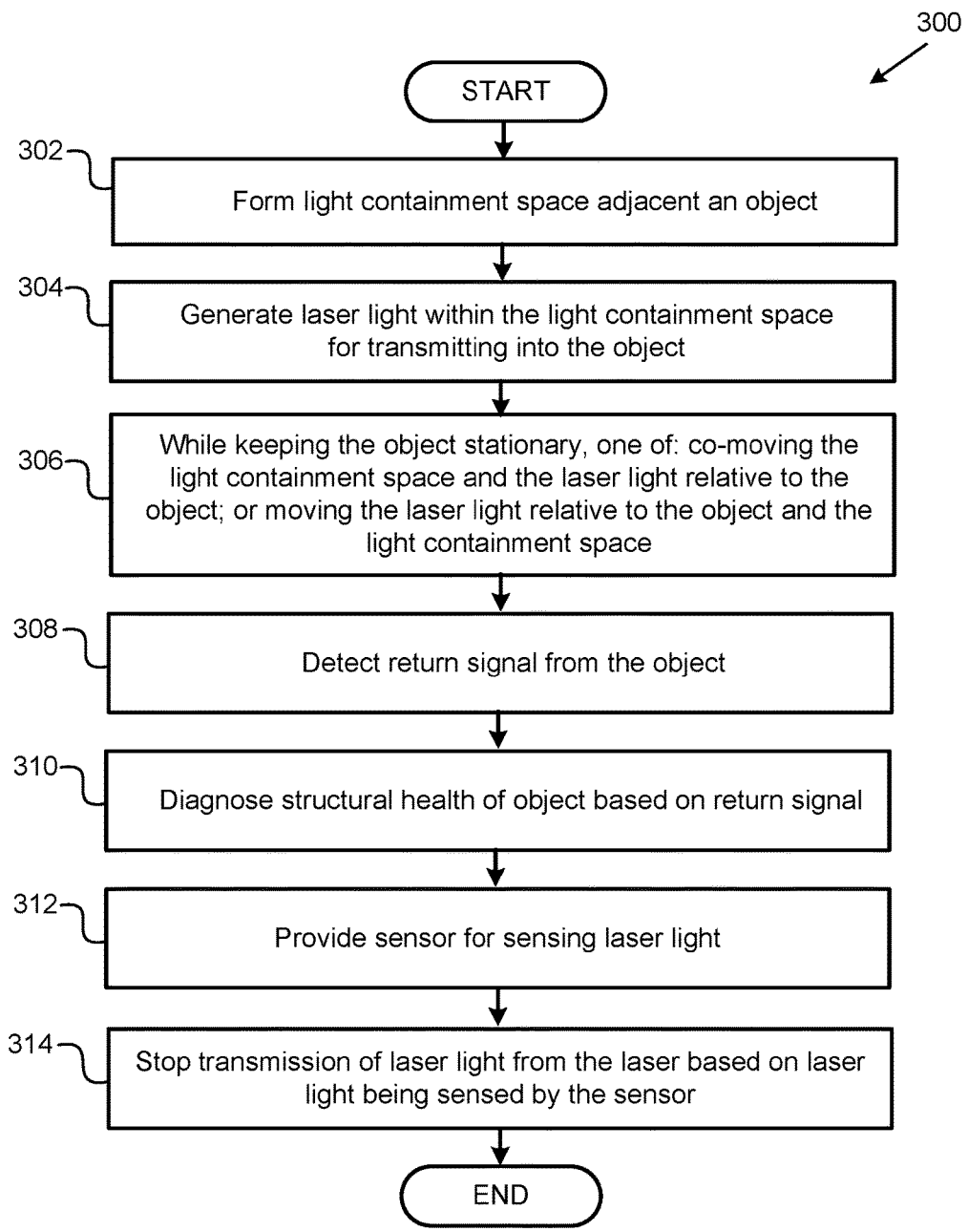
FIG. 8 is a schematic flow chart diagram illustrating a method of non-destructively inspecting an object, according to one or more embodiments of the present disclosure.

Referring to FIG. 8, according to one embodiment, a method 300 of non-destructively inspecting an object is shown. The method 300 includes forming a light containment space adjacent an object at 302. The light containment space can be formed using any of various systems and apparatuses described herein. The method 300 also includes generating a laser light within the light containment space for transmitting into the object at 304.

In one implementation, with the object kept stationary, the method 300 includes co-moving the light containment space and the laser light relative to the object. Such an implementation may be practiced using the system 100 shown in FIGS. 1-3. For example, forming the light containment space adjacent the object at 302 may include moving the apparatus 102 such that the object to be inspected is positioned or clamped between opposing portions 104A, 104B of the light shield 104. The apparatus 102 may be configured such that a distance between the first light seals 114A, 116A and the second light seals 114B, 116B is at least slightly less than a thickness of the object (e.g., a distance between the first surface 52 and the second surface 54) when the at least one biasing mechanism is in an unbiased state. As the apparatus 102 is slide over the object, to position the object between the opposing portions 104A, 104B of the light shield 104, the light seals 114A, 114B, 116A, 116B engage the object, which resiliently flexes the at least one biasing mechanism to bias the light seals against the object for promoting the seal between the light seals and the object. The entire apparatus 102, which defines the light containment space, is then moved along the object while the laser light within the light containment space is being generated and transmitted to the object.

According to another implementation, with the object kept stationary, the method 300 includes moving the laser light relative to the object and the light containment space at 306. Such an implementation may be practiced using any one of the systems 200, 201, 203 shown in FIGS. 4-7. For example, forming the light containment space adjacent the object at 302 may include moving the apparatus 202, such that the light shield 204, with light seals 214, 216, is pressed up against the object over a hole of the object and either the light shield module 281, another shield 207 and light seals 214, 216, the opaque barriers 294, or other light containment mechanism is positioned against the opposing part of the hole. Then, with the light shield 204, and the additional shield 207 or opaque barriers 294 if applicable, stationary relative to the object, the arm 262 is actuated to move the inspection assembly 205, while generating laser light, and the light shield module 281 if applicable, around the edge of the hole.

The method 300 further includes detecting a return signal from the object at 308. The return signal may be the reflected laser light beam 135 resulting from the reflection of the detection laser light beam 134 off of the object. Detection of the return signal may be facilitated by the light detector 137. Additionally, the method 300 includes diagnosing the structural health of the object based on the characteristics of the return signal at 310. For example, the return signal can be compared to a baseline or expected return signal with disparities between the baseline or expected return signal and the actual return signal indicated one or more structural defects.

Additionally, the method 300 includes providing at least one sensor for sensing laser light at 312 and, if the object is being inspected with laser light, stopping the transmission of laser light from the laser based on the laser light being sensed by the sensor at 314. Generally, in one implementation, the at least one sensor is positioned at a location external to the light containment space such that if light is detected by the sensor then light has escaped or leaked from the light containment space.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of objects does not imply that any or all of the objects are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of objects, means different combinations of one or more of the listed objects may be used and only one of the objects in the list may be needed. The object may be a particular object, thing, or category. In other words, "at least one of" means any combination of objects or number of objects may be used from the list, but not all of the objects in the list may be required. For example, "at least one of object A, object B, and object C" may mean object A; object A and object B; object B; object A, object B, and object C; or object B and object C. In some cases, "at least one of object A, object B, and object C" may mean, for example, without limitation, two of object A, one of object B, and ten of object C; four of object B and seven of object C; or some other suitable combination.

Unless otherwise indicated, the terms "first," "second," etc. are used herein merely as labels, and are not intended to impose ordinal, positional, or hierarchical requirements on the objects to which these terms refer. Moreover, reference to, e.g., a "second" object does not require or preclude the existence of, e.g., a "first" or lower-numbered object, and/or, e.g., a "third" or higher-numbered object.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing.

In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. An apparatus for shielding light generated by a laser during non-destructive inspection of an object, the apparatus comprising:
   a light shield at least partially enveloping the laser and defining a first opening through which light generated by the laser passes from the laser to the object, wherein the light shield is opaque and comprises:
   at least one first biasing mechanism;
   a first portion that defines the first opening;
   a second portion, spaced apart from the first portion, defining a second opening;
   at least one second biasing mechanism; and
   a spine coupling together the first portion and the second portion;
   at least one first light seal coupled to the light shield about the first opening of the light shield, wherein the at least one first light seal is resiliently flexible and opaque; and
   at least one second light seal coupled to the second portion of the light shield about the second opening;
   wherein:
   the object comprises a first surface, a second surface opposing the first surface, and an edge at a convergence of the first surface and the second surface;
   the at least one first biasing mechanism is configured to urge resilient deformation of the at least one first light seal against the first surface of the object;
   the at least one second biasing mechanism is configured to urge resilient deformation of the at least one second light seal against the second surface of the object; and
   when the at least one first light seal is resiliently deformed against the first surface of the object and the at least one second light seal is resiliently deformed against the second surface of the object, light generated by the laser is constrained within a light containment space defined between the light shield, the at least one first light seal, the at least one second light seal, and the object.

2. The apparatus of claim 1, wherein the light shield and the at least one first light seal is movable relative to the object when the at least one first light seal is resiliently deformed against the object.

3. The apparatus of claim 1, wherein the at least one first biasing mechanism of the light shield comprises at least one concertinaed sidewall of the light shield.

4. The apparatus of claim 1, further comprising a hinge, wherein:
   at least a portion of the light shield is pivotable about the hinge; and
   the at least one first biasing mechanism comprises at least one spring configured to pivotally bias the at least a portion of the light shield about the hinge.

5. The apparatus of claim 1, further comprising at least one light sensor, wherein the at least one first light seal is positioned between the at least one light sensor and the first opening defined by the light shield.

6. The apparatus of claim 1, wherein the at least one first light seal is a first inner light seal and a first outer light seal, the first inner light seal being spaced apart from the first outer light seal.

7. The apparatus of claim 6, further comprising at least one inner light sensor and at least one outer light sensor, wherein:
   the first inner light seal is positioned between the at least one inner light sensor and the first opening defined by the light shield; and
   the first outer light seal is positioned between the at least one inner light sensor and the at least one outer light sensor.

8. The apparatus of claim 1, wherein the laser is non-movably fixed to the light shield.

9. The apparatus of claim 1, wherein:
   the laser is movably fixed to the light shield; and
   the light shield is movable relative to the object.

10. The apparatus of claim 1, further comprising a light sensor fixed relative to the second portion of the light shield, spaced apart from the laser, and aligned to receive light directly from the laser when the light is unobstructed by the object.

11. The apparatus of claim 1, wherein the light shield comprises:
    a rigid frame; and
    a flexible and an opaque material affixed to the rigid frame.

12. An apparatus for shielding light generated by a laser during non-destructive inspection of an object, the apparatus comprising:
    a light shield at least partially enveloping the laser and defining a first opening through which light generated by the laser passes from the laser to the object, wherein the light shield is opaque and comprises at least one first biasing mechanism; and
    at least one first light seal coupled to the light shield about the first opening of the light shield, wherein the at least one first light seal is resiliently flexible and opaque;
    wherein:
    the at least one first biasing mechanism is configured to urge resilient deformation of the at least one first light seal against the object; and when the at least one first light seal is resiliently deformed against the object, light generated by the laser is constrained within a light containment space defined between the light shield, the at least one first light seal, and the object;
the light shield has a substantially circular cross-sectional shape;
the at least one first light seal has a substantially annular shape;
the object comprises a first surface, a second surface opposing the first surface, and an edge at a convergence of the first surface and the second surface;
the at least one first biasing mechanism is configured to urge resilient deformation of the at least one first light seal against the first surface of the object; and
the apparatus further comprises a light shield module fixed relative to the laser and movable relative to the light shield, wherein the light shield module comprises:
  a bracket positionable to wrap around the edge of the object from the first surface to the second surface;
  at least one second light seal coupled to the bracket; and
  at least one second biasing mechanism configured to urge resilient deformation of the at least one second light seal against the second surface of the object.

13. The apparatus of claim 12, wherein:
the object comprises a first surface, a second surface opposing the first surface, and an edge at a convergence of the first surface and the second surface;
the at least one first biasing mechanism is configured to urge resilient deformation of the at least one first light seal against the first surface of the object;
the light shield is a first shield;
the apparatus further comprises:
  a second light shield that is independently movably relative to the first shield, is opaque, defines a second opening, has a substantially circular cross-sectional shape, and comprises at least one second biasing mechanism; and
  at least one second light seal coupled to the second light shield about the second opening of second shield, wherein the at least one second light seal is resiliently flexible and opaque;
the at least one second biasing mechanism is configured to urge resilient deformation of the at least one second light seal against the second surface of the object; and
when the at least one first light seal is resiliently deformed against the first surface of the object and the at least one second light seal is resiliently deformed against the second surface of the object, the light containment space is defined between the first shield, the at least one first light seal, the at least one second light seal, the second shield, and the object.

14. The apparatus of claim 12, wherein:
the object comprises a first surface, a second surface opposing the first surface, and an edge at a convergence of the first surface and the second surface;
the at least one first biasing mechanism is configured to urge resilient deformation of the at least one first light seal against the first surface of the object;
the apparatus further comprises an opaque light barrier, independently movable relative to the light shield and positionable against the second surface of the object; and
when the at least one first light seal is resiliently deformed against the first surface of the object and the opaque light barrier is positioned against the second surface of the object, the light containment space is defined between the light shield, the at least one first light seal, the opaque light barrier, and the object.

15. An apparatus for shielding light generated by a laser during non-destructive inspection of an object, the apparatus comprising:
a light shield at least partially enveloping the laser and defining a first opening through which light generated by the laser passes from the laser to the object, wherein the light shield is opaque and comprises at least one first biasing mechanism; and
at least one first light seal coupled to the light shield about the first opening of the light shield, wherein the at least one first light seal is resiliently flexible and opaque;
wherein:
  the at least one first biasing mechanism is configured to urge resilient deformation of the at least one first light seal against the object;
  when the at least one first light seal is resiliently deformed against the object, light generated by the laser is constrained within a light containment space defined between the light shield, the at least one first light seal, and the object; and
  the at least one first biasing mechanism of the light shield comprises at least one concertinaed sidewall of the light shield.

16. An apparatus for shielding light generated by a laser during non-destructive inspection of an object, the apparatus comprising:
a light shield at least partially enveloping the laser and defining a first opening through which light generated by the laser passes from the laser to the object, wherein the light shield is opaque and comprises at least one first biasing mechanism;
at least one first light seal coupled to the light shield about the first opening of the light shield, wherein the at least one first light seal is resiliently flexible and opaque; and
a hinge;
wherein:
  the at least one first biasing mechanism is configured to urge resilient deformation of the at least one first light seal against the object;
  when the at least one first light seal is resiliently deformed against the object, light generated by the laser is constrained within a light containment space defined between the light shield, the at least one first light seal, and the object;
  at least a portion of the light shield is pivotable about the hinge; and
  the at least one first biasing mechanism comprises at least one spring configured to pivotally bias the at least a portion of the light shield about the hinge.

* * * * *